Figure 1:
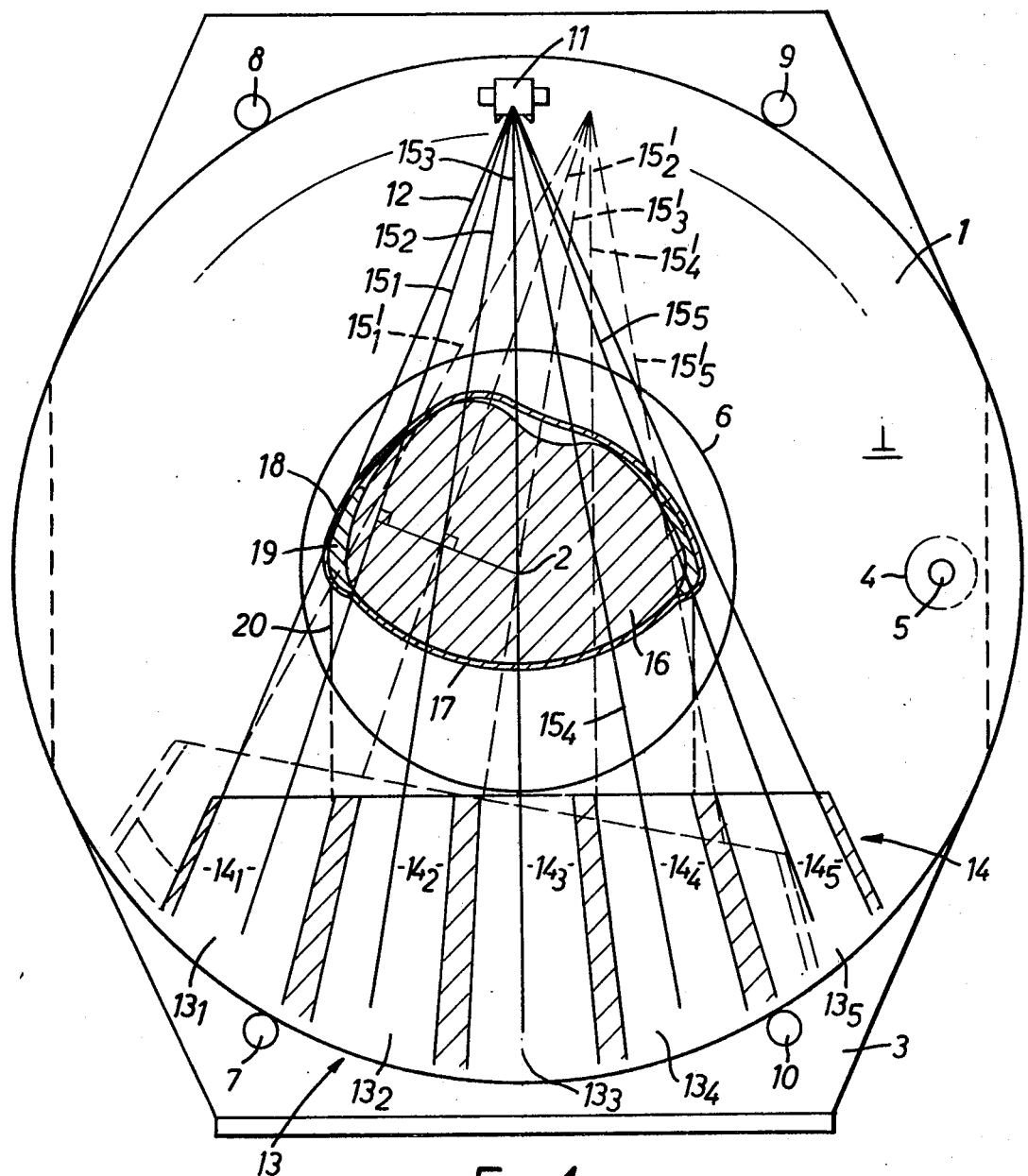

United States Patent [19]
Hounsfield

[11] 4,138,611
[45] Feb. 6, 1979

[54] FAN BEAM CT APPARATUS WITH POST-PROCESSING WEIGHTING OF PICTURE ELEMENT SIGNALS

[75] Inventor: Godfrey N. Hounsfield, Newark, England

[73] Assignee: EMI Limited, Hayes, England

[21] Appl. No.: 793,390

[22] Filed: May 3, 1977

[30] Foreign Application Priority Data

May 13, 1976 [GB] United Kingdom ............. 19681/76

[51] Int. Cl.² ............................................. A61B 6/02
[52] U.S. Cl. ................................. 250/445 T; 250/360
[58] Field of Search .......................... 250/360, 445 T

[56] References Cited
U.S. PATENT DOCUMENTS 3,881,110  4/1975  Hounsfield et al. ................ 250/360

*Primary Examiner*—Alfred E. Smith
*Assistant Examiner*—T. N. Grigsby

*Attorney, Agent, or Firm*—Cooper, Dunham, Clark, Griffin & Moran

[57] ABSTRACT

In a computerized tomographic apparatus in which a wide angled, fan-shaped distribution of radiation is rotated around a body to be radiographed and detectors are provided to produce electrical output signals indicative of radiation emergent from the body along many beam paths, the signals can be sorted into sets relating to parallel sets of beam paths distributed across a cross-sectional slice of the body. However, the beam paths to which the signals so sorted relate are non-uniformly spaced beam paths, and the invention provides means whereby a processing technique known as convolution, which is of proven usefulness in computerized tomography but which, for best accuracy, operates upon output signals relating to sets of uniformly spaced, parallel beam paths, can be applied to the signals as sorted and a post-processing error compensation is effected to restore accuracy.

8 Claims, 2 Drawing Figures

FAN BEAM CT APPARATUS WITH POST-PROCESSING WEIGHTING OF PICTURE ELEMENT SIGNALS

The present invention relates to radiography, and it relates more particularly to that branch of radiography which has become known as computerised axial tomography, or briefly C.A.T. Apparatus for performing C.A.T. has the aim of producing a representation of the absorption coefficients, with respect to penetrating radiation, at a plurality of elemental locations distributed over a cross-sectional slice of a body under investigation. Such apparatus is disclosed and claimed in U.S. Pat. No. 3,778,614.

The technique of performing C.A.T. involves deriving signals indicative of the absorption suffered by penetrating radiation, such as X-radiation, on traversing many beam paths through the aforementioned slice of the body and in alignment with said slice. These signals are then processed to evaluate the aforementioned coefficients.

In order to project the radiation through the slice along the many beam paths referred to above, a source of one or more beams of the radiation is scanned, relative to the body, around the outside of the slice. If the source produces just one pencil-like beam of radiation, or if it produces a number of mutually divergent beams within a fan-shaped distribution of relatively small angular spread, such as 10°, it is usual for the scanning to consist of alternate lateral traverses, during which the source is scanned from one side to the other across the body, and rotational steps. Such scanning is described in more detail in the aforementioned U.S. Pat. No. 3,778,614 and in U.S. Pat. No. 3,946,234.

The present invention, however, has especial relevance to circumstances when more rapid scanning is desired, and the source is arranged to produce a fan-shaped distribution of radiation which has a considerable angular spread, such as 30° or more, so that the scanning can be effected by mere rotation of the source around the body, about an axis intersecting the aforementioned slice. The lateral scanning can be omitted because the angular spread of the distribution of radiation is sufficient to encompass at least a substantial part of the slice.

In order that signals indicative of the absorption suffered by the radiation on traversing each of said paths can be determined, it is necessary to detect the amount of radiation emergent from the body along each path. This can be done, for example, by means of an array of radiation detectors, distributed across the breadth of the distribution of radiation, disposed at the opposite side of the body to the source, and arranged to rotate, with the source, around the body. The detectors are arranged to provide electrical output signals indicative of the amounts of radiation emergent from the body along the various beam paths; output signals relating to adjacent paths viewed by the same detector being segregated by periodic sampling, typically effected by reading and re-setting of integrator circuits to which the detectors are coupled. The reading and re-setting occurs at a rate which is considerably higher than that at which the source and detectors rotate around the body.

It will be appreciated that, in the above circumstances, each detector always receives radiation projected along a respective beam within the spread; the beams being equi-angularly spaced. As the source and the detectors are rotated relative to the body, each detector is repeatedly sampled at intervals which correspond to rotational movements corresponding to the inter-beam angle, and by this means a sequence of signals indicative of the absorption suffered by the radiation on traversing each of a group of beam paths is derived from each detector. The group of beam paths to which the signals derived from any one detector relate will not, of course, be parallel to one another; they will be angularly spaced from one another at substantially the aforementioned inter-beam angle. These paths are, however, characterised by having a common perpendicular distance to the axis of the rotational scan.

It is convenient to process the signals derived from all of the detectors by means of the technique of convolution described and claimed in U.S. Pat. No. 3,924,129 but this technique is most conveniently and accurately applied to output signals relating to sets of equally spaced, parallel beam paths.

The signals obtained as described above can be sorted into sets relating to parallel beam paths; it being appreciated that the signals of a set are all derived from different detectors and obtained at different times during the scanning. However these beam paths are not equally spaced and when it is desired to evaluate the aforementioned coefficients with high accuracy, it has been found necessary to allow for this lack of equal spacing, which arises because the perpendicular distances to the axis of rotation for the various detectors vary in a substantially sinusoidal fashion from the axis outwards; the paths being more closely spaced towards the edges of the region of interest than they are at the centre thereof.

The above-mentioned inequality of beam spacing occurs also when the detectors are not rotated, with the source, around the body under examination but instead are fixed and distributed around a circular path centred on said axis of rotation. More detectors are required in this case because instead of merely extending across the breadth of the fan-shaped distribution of radiation, it is necessary for the detectors to be sufficient to subtend an angle, at the said axis, of at least 180° plus the angle of the distribution of radiation. Preferably the detector array subtends a full 360° angle at said axis.

The object of this invention is to allow for the aforementioned inequality of beam spacing.

According to the invention there is provided radiographic apparatus including a source of a fan-shaped distribution of penetrating radiation, support means supporting said source so that said radiation propagates through a predetermined region, which region, in operation of the apparatus, is occupied by a selected cross-sectional slice of an object to be radiographed, means for moving said support means, and with it said source, angularly around said region, about an axis intersecting said region, so that said radiation propagates through said region from a plurality of different directions, detector means for detecting radiation emergent from said region along a plurality of mutually divergent beam paths from each of said directions, and for producing electrical output signals indicative of the amounts of radiation emergent from said region along the various beam paths, sorting means for sorting said electrical signals into sets relating to respective sets of substantially parallel beam paths through said region, and compensating means for allowing for lack of uniformity of spacing between adjacent beam paths of said sets, said compensating means including means for deriving from said electrical output signals, by a process of convolution, values of the absorption coefficient, with respect to said radiation, appropriate to each element of an array of elements notionally delineated in said slice of said object, means for producing a respective compensating factor appropriate for each of said elements and indicative of error in said derived values and attributable to said lack of uniformity of spacing, and means for combining corresponding ones of said derived values and said compensating factors to produce a representation of the said absorption coefficients in which said error is reduced.

Figure 2:
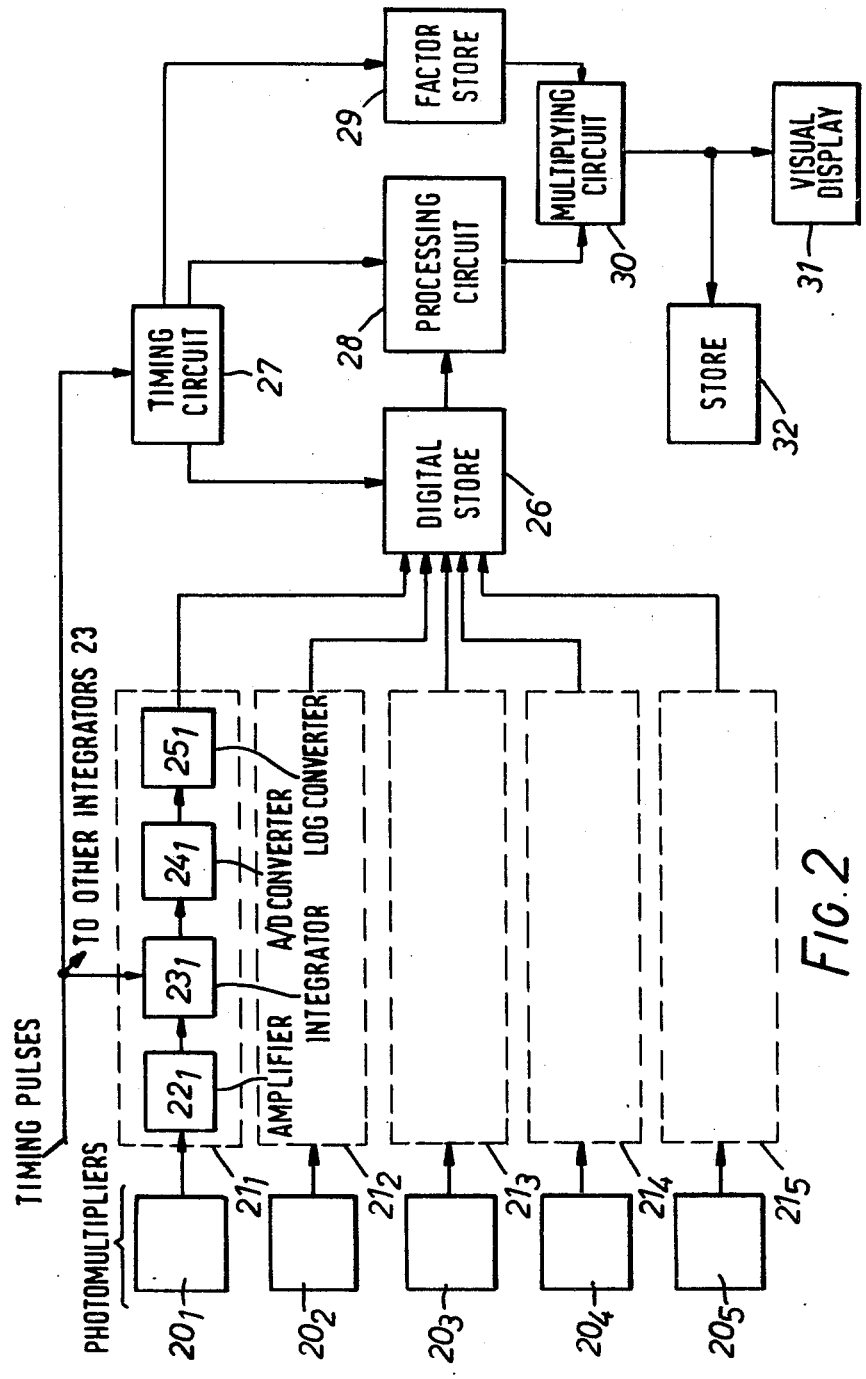

In order that the invention may be clearly understood and readily carried into effect, some embodiments thereof will now be described with reference to the accompanying drawings, of which FIG. 1 shows, in front elevational view, some of the components of the C.A.T. apparatus in which the only mechanical scanning movement is a rotational one, and shows how the aforementioned non-uniformity of spacing of parallel beam paths occurs, and FIG. 2 shows circuits for accepting output signals from the apparatus shown in FIG. 1, and operating upon them in accordance with one example of the invention.

Referring now to FIG. 1, a ring-like rotatable support structure 1, is mounted for rotation about an axis 2. The structure 1 comprises an annular member which can be rotated relative to a static main frame 3 by an electric motor 4. The motor 4 is mounted on the main frame 3 and drives a gear wheel 5 which co-operates with gear teeth (not shown) formed all around the inner periphery of the ring-like structure 1. The main frame 3 has an aperture 6 formed therein, the aperture 6 being concentric with the ring-like structure 1, and also supports a number of guides 7, 8, 9, 10 which act as bearings during rotation of structure 1 about the axis 2 and thus support the load of that structure; the guides 7 through 10 being also formed with flanges to limit fore-and-aft movement of the structure 1.

The structure 1 supports an X-ray tube 11, arranged to produce a planar fan-shaped distribution 12 of X-radiation, and a bank 13 of detectors, the detectors being sensitive to said radiation and being distributed across the breadth of the distribution 12. The individual detectors, which may comprise thallium activated sodium iodide crystals, are numbered $13_1$, $13_2$ ... $13_5$; only five detectors being shown in this case for clarity, although more typically, for a fan-shaped distribution of angle 40° as shown, 120 detectors would be used, adjacent detectors being angled at $\frac{1}{3}$° to each other. Each detector in the array 13 views the radiation source 11 through a respective collimator 14 so as to reduce the amount of scattered radiation received by the detectors and thus each detector receives radiation along a respective beam 15 in the distribution 12; the beams being indicated in the drawing by their centre lines, although it will be appreciated that the beams are actually of finite width as determined by the collimator and detector dimensions. It will also be appreciated that, in this example, and prior to its incidence upon the collimators 14, the distribution 12 is continuous across its breadth. This need not be the case, however, and the radiation distribution could, if desired, be sectioned up into beams prior to its incidence on the body.

The body 16 to be examined is supported on a bed 17 and held firmly thereon by means of a strap 18 secured to the sides of the bed. Packing material 19 is inserted in gaps between the body and the bed in order to reduce, so far as is possible, the entrapments of air between the patient and the bed. The material 19 is preferably contained in one or more flexible bags and absorbs the radiation to an extent similar to human body tissue. The bed is supported on either side of the main frame 3; one of the supports being shown at 20. It will be appreciated, of course that the aperture 6 in the main frame 3 must be sufficiently large to enable the body 16 to be positioned as required relative to the distribution 12.

As will be seen, when the structure 1 is in the position shown in the drawing, so that the source 11 projects the distribution 12 through the body from the direction indicated in solid lines, each of the beams 15 traverses a respective path through the body 16, and the corresponding detector 13 provides an output signal indicative of the absorption suffered by the radiation on traversing the relevant path. In practice, an output signal relates not to a beam as irradiated from a single point, but to a broader beam path irradiated during rotation of the structure 1 through a finite angle. This matter, however, will be ignored henceforth, because it is not relevant to the understanding of the invention, and it will be assumed that the output signals relate to beam paths irradiated at unique angular positions of the structure 11.

It will be observed that the various beams 15, and consequently the corresponding beam paths through the body, diverge from one another to equal angles and so the group of output signals obtained in any one position of the structure 1 do not relate to a parallel set of beam paths.

If the structure 1 is rotated through an angle corresponding to the angle between adjacent beams 15, so that the swath 12 assumes the position indicated by dotted lines, then the beams 15 will irradiate a new group of beam paths through the body 16. In this case, the beam path $15_2'$ viewed by detector $13_2$ from its new position is parallel with the beam path $15_1$ which was viewed by detector $13_1$ in its original position. Likewise the path $15_3'$ which was viewed by detector $13_3$ in its new position is parallel to the path $15_2$ viewed by detector $13_2$ in its original position, and so on. Further rotational movement of the structure 1 about the axis 2 causes the various detectors to provide output signals relating to beam paths parallel to paths for which output signals have previously been provided by other detectors. Typically the angular movement of the structure 1 takes place through an angle which substantially equals or exceeds the sum of 180° and the fan angle; the object being to obtain signals relating to sets containing equal numbers of parallel beam paths, the sets being uniformly distributed in angle over 180°.

As the mechanical movement is purely rotational, however, the beam paths of a parallel set are not uniformly spaced across the irradiated region of the body. This can be seen by comparing the perpendicular distance from the axis 2 to two parallel beam paths as irradiated by beams $15_1$ (detected by detector $13_1$) and $15'_2$ (detected by detector $13_2$), the structure 1 having rotated through an angle corresponding to the inter-beam angle between the irradiation of the two beam paths. If the distance from the point source of x-rays, within tube 11, to the axis 2 is designated $r$, and if the inter-beam angle is 10°, then the perpendicular distances from axis 2 to beams $15_1$ and $15_2'$ respectively are $r \sin 20°$ and $r \sin 10°$ respectively. Since the third beam of the parallel set in question will pass through the axis 2 and be detected by detector $13_3$ after the structure 1 has rotated through a further 10°, it will be seen that the values $r \sin 10°$ and $r(\sin 20° - \sin 10°)$ represent the distances between respective pairs of beam paths in a parallel set and that these distances are not equal. Clearly the same thing will happen for beam paths on the other side of the axis 2 to those irradiated by beams $15_1$ and $15_2'$, and clearly also the non-uniformity of distance will be the same for all parallel sets of beam paths. For a fan angle of 40°, the overall departure from uniformity of spacing amounts to some 3% and, if it is desired to use a processing technique of the convolution kind described and claimed in the aforementioned U.S. Pat. No. 3,924,129 and if it is desired to evaluate the aforementioned absorption coefficients with high accuracy, this departure should be allowed for. FIG. 2 indicates one way in which this can be achieved.

In FIG. 2 there are shown blocks $20_1, 20_2...20_5$ which represent photomultiplier tubes disposed to receive the light output from respective ones of the detectors 13 (see FIG. 1). Each photomultiplier feeds a respective pre-processing circuit 21, of which only the circuit $21_1$, associated with photomultiplier $20_1$, is shown in detail since the others are all the same.

The circuit $21_1$ comprises four components, namely an amplifier $22_1$, an integrator $23_1$, an analogue-to-digital converter $24_1$ and a logarithmic converter circuit $25_1$; all of these circuits being of conventional construction. The integrators such as $23_1$ are all read and reset periodically, at times related to the rotation of the structure 1 (FIG. 1) through the inter-beam angle. As mentioned previously, in the simplified example shown the inter-beam angle is 10°, but a more realistic inter-beam angle, as used in practice, is $\frac{1}{3}°$. The integrators are read and reset by timing pulses generated in known manner by the progress of graticule markings carried by the structure 1 (FIG. 1) past a fixed photocell and detector unit (not shown).

The signals issuing from the pre-processing circuits 21 are applied to a random access digital store 26, whence they can be derived, under the influence of timing pulses generated by a main timing circuit 27, in groups relating to parallel sets of beam paths. These paths, as has been established, are not equally spaced apart, but nevertheless the groups of signals relating thereto are applied to a convolution processing circuit 28, which is of the kind described and claimed in U.S. Pat. No. 3,924,129 and which processes the groups of signals as if they did relate to uniformly spaced sets of parallel beam paths. Thus absorption coefficients are evaluated which are applicable to various locations distributed over the examined slice of the body 16, though these evaluated coefficients are potentially in error because no account has been taken of the aforementioned non-uniformity of beam path spacing.

In accordance with this example of the invention, the body 16 is replaced by a phantom having a known absorption coefficient at each of the locations corresponding to the locations for which evaluation is effected by the apparatus. The phantom is scanned by the apparatus, as previously described, and the circuit 28 evaluates the absorption coefficients applicable to the various locations distributed over the phantom. The evaluated coefficient for each location is compared with the known coefficient for that location to ascertain, for each location, a multiplying factor which, when multiplied by the evaluated coefficient for the location, equals the known coefficient for the location. The multiplying factors so evaluated are stored in a digital store 29 and are used when the apparatus scans a real body to compensate for the errors mentioned above. The store 29 is controlled by the main timing circuit 27 and is effective to apply the multiplying factors, in a predetermined sequence, to a multiplying circuit 30 with correct timing to multiply the evaluated coefficients relating to the respective locations. The corrected coefficients are applied to a visual display device 31, such as a cathode ray tube with facilities for photographing the image displayed thereon, and to a long term store 32, such as a magnetic tape or disc store. Usefully, the device 31 contains means of known kind for varying the mean level and/or the dynamic range of signals displayed thereby.

The invention may also be applied to apparatus of the kind described in U.S. application Ser. No. 630,779, now U.S. Pat. No. 4,010,370, or in U.S. application Ser. No. 733,941, filed Oct. 19, 1976, in which, in addition to the rotational mechanical motion imparted to the source and detectors, the X-ray tube contains means for deflecting the electron beam thereof over an elongated anode so as to effectively provide a limited (e.g. 2.5cm to 10cm) translational movement of the spread 12 of radiation relative to the body.

If required, as mentioned in the introductory paragraphs of this specification, the detectors 13 need not participate in the rotational movement, but instead they may be fixed and distributed around a more extensive circular path centred on the axis 2. Typically, the circular path is of large enough diameter to permit tube 11 to rotate inside it.

The phantom preferably is constructed of material, such as that known by the Registered Trade Mark "Perspex", having similar absorption properties to the mean absorption of human tissue. The phantom may be constructed to have substantially constant absorption over the whole of the cross-sectional slice thereof which is irradiated. Alternatively, the phantom may comprise annular bands of different radii and different absorption characteristics, the bands being arranged contiguously with one another to form a continuous body.

The correction effected by means of the invention constitutes, in effect, a post-processing re-alignment of beam paths. It will be appreciated that the magnitudes of the errors, due to the non-uniformity of beam path spacing, which would otherwise occur would not constitute gross misalignment of true beam paths with those assumed for the purposes of processing, but that the errors could affect the evaluation of absolute absorption coefficients over part at least of the body slice.

What I claim is:

1. Radiographic apparatus including a source of a fan-shaped distribution of penetrating radiation, support means supporting said source so that said radiation propagates through a predetermined region, which region, in operation of the apparatus, is occupied by a selected cross-sectional slice of an object to be radiographed, means for moving said support means, and with it said source, angularly around said region, about an axis intersecting said region, so that said radiation propagates through said region from a plurality of different directions, detector means for detecting radiation emergent from said region along a plurality of mutually divergent beam paths from each of said directions, and for producing electrical output signals indicative of the amounts of radiation emergent from said region along the various beam paths, sorting means for sorting said electrical signals into sets relating to respective sets of substantially parallel beam paths through said region, and compensating means for allowing for lack of uniformity of spacing between adjacent beam paths of said sets, said compensating means including means for deriving from said electrical output signals, by a process of convolution, values of the absorption coefficient, with respect to said radiation, appropriate to each element of an array of elements notionally delineated in said slice of said object, means for producing a respective compensating factor appropriate for each of said elements and indicative of error in said derived values and attributable to said lack of uniformity of spacing, and means for combining corresponding ones of said derived values and said compensating factors to produce a representation of the said absorption coefficients in which said error is reduced.

2. Apparatus according to claim 1 wherein said means for producing compensating factors includes means for locating a phantom body, of known absorption characteristics, in said region, means causing said apparatus to scan said phantom body and to process the electrical output signals provided during the scanning to produce an estimate of said absorption characteristics, and means for comparing estimated and known absorption values for corresponding elements of said phantom body to produce said compensating factors.

3. Apparatus according to claim 1 wherein said detector means comprises an array of detectors extending across said fan-shaped distribution of radiation and mounted upon said support means so as to partake in said angular movement with said source.

4. Apparatus according to claim 1 wherein said means for combining comprises a multiplying circuit.

5. Apparatus according to claim 1 wherein the means for producing compensating factors comprise means for storing, for each of said elements of the array, a compensating factor which is a function of any difference between the absorption coefficient derived by said deriving means for the corresponding element of a phantom having a known absorption coefficient for said element and the known absorption coefficient of said element of the phantom.

6. A medical diagnostic X-ray machine for examining a slice of a patient which extends along a planar section through the patient, comprising:

means for generating X-radiation directed along said section at the patient from locations distributed along an orbit which extends at least half way around the patient and is along the section, and means for measuring the radiation from each location which has passed through the patient along said section in beam paths fanning out from the location and for producing measurements signals each related to the radiation measured by the measuring means at a respective beam path;

means for deriving, from the measurement signals, sequences of measurement signals related to sets of beam paths in which the paths of a set are substantially parallel to each other and are at an angle to the paths of any other set;

means for receiving the sequences of measurement signals and for converting each given measurements signal into a corrected measurement signal which is a function of the given measurement signal and of every other measurement signal of the same sequence;

means for forming a picture element signal for each of the elements into which the patient slice is divided by a finite Cartesian matrix notionally superimposed on the slice, each picture element signal being a function of the corrected measurement signals related to beam paths passing through the corresponding slice element and representing the X-ray response of the element;

means for providing a compensating factor for each of at least a substantial subset of the patient slice elements and means for weighting the picture element signals in accordance with the compensating factors for the respective patient slice elements to thereby produce compensated picture element signals, and means for displaying the compensated picture element signals to thereby display a picture of the anatomy of the patient slice examined with the machine.

7. A medical diagnostic X-ray machine as in claim 6 which the means for providing the compensating factors include means for producing compensating factors which account for differences in spacing between the adjacent beam paths of each set of parallel beam paths.

8. A medical diagnostic X-ray machine as in claim 6 in which the means for deriving the compensating factors include means for disposing a phantom of known X-ray response at said section, in place of the patient slice, means for causing the generating, measuring, producing, deriving, receiving and forming means to form first picture element signals for the elements into which the phantom slice along the section is divided by said matrix and means for comparing the first picture element signal with the known X-ray response of the phantom and for producing said compensation factors on the basis thereof.

* * * * *